(12) United States Patent
Kalsi et al.

(10) Patent No.: US 12,064,409 B2
(45) Date of Patent: Aug. 20, 2024

(54) ACTION OF L-CITRULLINE TO PREVENT OR TREAT ENDOTHELIAL DYSFUNCTION

(71) Applicants: Asklepion Pharmaceuticals, LLC, Baltimore, MD (US); Vanderbilt University, Nashville, TN (US)

(72) Inventors: Gurdyal Kalsi, Potomac, MD (US); Frederick Barr, Little Rock, AR (US); Gary Pasternack, Baltimore, MD (US); Marshall Summar, Washington, DC (US)

(73) Assignees: VANDERBILT UNIVERSITY, Nashville, TN (US); ASKLEPION PHARMACEUTICALS, LLC, Baltimore, MD (US)

( * ) Notice: Subject to any disclaimer, the term of this patent is extended or adjusted under 35 U.S.C. 154(b) by 410 days.

(21) Appl. No.: 17/364,280

(22) Filed: Jun. 30, 2021

(65) Prior Publication Data

US 2022/0401396 A1    Dec. 22, 2022

Related U.S. Application Data

(60) Provisional application No. 63/213,600, filed on Jun. 22, 2021.

(51) Int. Cl.
*A61K 31/198* (2006.01)
*A61P 11/00* (2006.01)
*A61P 31/14* (2006.01)

(52) U.S. Cl.
CPC ............ *A61K 31/198* (2013.01); *A61P 11/00* (2018.01); *A61P 31/14* (2018.01)

(58) Field of Classification Search
CPC .......... A61K 31/198; A61P 11/00; A61P 31/14
See application file for complete search history.

(56) References Cited

U.S. PATENT DOCUMENTS

| | | | |
|---|---|---|---|
| 9,486,429 B2 | 11/2016 | Summar et al. | |
| 10,265,286 B2 | 4/2019 | Summar et al. | |

(Continued)

OTHER PUBLICATIONS

Gielis et al., "Pathogenetic role of eNOS uncoupling in cardiopulmonary disorders", Free Radical Biology& Medicine,2011,50:765-776. (Year: 2011).*

(Continued)

*Primary Examiner* — Deborah D Carr
(74) *Attorney, Agent, or Firm* — ArentFox Schiff LLP

(57) ABSTRACT

This invention provides methods for treating endothelial dysfunction by administering an effective amount of citrulline to a patient. The patients may be suffering from acute respiratory distress syndrome (ARDS), sepsis, or infection by COVID-19 (Coronavirus Disease 2019); COVID-19 patients may be at risk of developing endothelial dysfunction, or they may be experiencing endothelial dysfunction. The effective amount of citrulline is sufficient to reduce the uncoupling of endothelial nitric oxide synthase (eNOS) or to reduce the formation of free radicals. Citrulline may be administered orally; intravenously; or both orally and intravenously in a sequential manner. Sequential administration of citrulline may be in three phases, such as (a) an initial phase in which citrulline is administered orally, (b) an intermediate phase wherein citrulline is administered intravenously, and (c) a final phase wherein citrulline is administered orally. The intermediate phase may be while the patient's breathing is being assisted mechanically.

20 Claims, 3 Drawing Sheets

(56) References Cited

U.S. PATENT DOCUMENTS

| | | | |
|---|---|---|---|
| 10,525,026 | B2 | 1/2020 | Summar et al. |
| 2004/0186164 | A1 | 9/2004 | Kaesemeyer |
| 2009/0312423 | A1 | 12/2009 | Summar et al. |
| 2011/0044965 | A1* | 2/2011 | Greco ............... A61P 15/10 514/564 |
| 2018/0289647 | A1 | 10/2018 | Summar et al. |
| 2019/0091194 | A1 | 3/2019 | Chin et al. |

OTHER PUBLICATIONS

Gavriilaki et al., "Endothelial Dysfunction in COVID-19: Lessons Learned from Coronaviruses",Curr Hypertens Rep.,2020,22:63. (Year: 2020).*

Li, et al. SARS-CoV-2 and viral sepsis: observations and hypotheses. Lancet. 2020;395:1517-20.

Fox, et al. Pulmonary and cardiac pathology in African American patients with COVID-19: an autopsy series from New Orleans. Lancet Respir Med. 2020.

Buja, et al. The emerging spectrum of cardiopulmonary pathology of the coronavirus disease 2019 (COVID-19): Report of 3 autopsies from Houston, Texas, and review of autopsy findings from other United States cities. Cardiovasc Pathol. 2020;48:107233.

Ackermann, et al. Pulmonary Vascular Endothelialitis, Thrombosis, and Angiogenesis in Covid-19. N Engl J Med 2020.

Schaller, et al. Postmortem Examination of Patients With COVID-19. Jama. 2020.

Wichmann, et al. Autopsy Findings and Venous Thromboembolism in Patients With COVID-19. Ann Intern Med. 2020:E1-E3.

Mahmoud-Elsaye, et al. Echocardiographic Findings in Covid-19 Pneumonia. Can J Cardiol. 2020:1203-1207.

Chen, et al. The ACE2 expression in human heart indicates new potential mechanism of heart injury among patients infected with SARS-CoV-2. Cardiovasc Res. 2020;116.

Carnevale, et al. Direct endothelial damage and vasculitis due to SARS-CoV-2 in small bowel submucosa of CoViD-19 patient with diarrhea. J Med Virol. 2020:61-63.

Teuwen, et al. COVID-19: the vasculature unleashed. Nat Rev Immunol. 2020:1-3.

Connors, et al. COVID-19 and its implications for thrombosis and anticoagulation. Blood. 2020;135:2033-40.

Iba, et al. Coagulopathy of Coronavirus Disease 2019. Crit Care Med. 2020.

Boisramé-Helms, et al. Endothelial dysfunction in sepsis. Curr Vasc Pharmacol. 2013;11:150-60.

Pons, et al. Immune Consequences of Endothelial Cells' Activation and Dysfunction During Sepsis. Crit Care Clin. 2020;36:401-13.

Smadja, et al. Angiopoietin-2 as a marker of endothelial activation is a good predictor factor for intensive care unit admission of COVID-19 patients. Angiogenesis. 2020:1-10.

Li, et al. D-dimer triage for COVID-19. Acad Emerg Med. 2020.

Cummings, et al. Epidemiology, clinical course, and outcomes of critically ill adults with COVID-19 in New York City: a prospective cohort study. Lancet. 2020;395:1763-70.

Gustafson, et al. Overcoming Barriers: The Endothelium As a Linchpin of Coronavirus Disease 2019 Pathogenesis? Arterioscler Thromb Vasc Biol. 2020:1-12.

Cyr, et al. Nitric Oxide and Endothelial Dysfunction. Crit Care Clin. 2020;36:307-21.

Tousoulis, et al. The role of nitric oxide on endothelial function. Curr Vasc Pharmacol. 2012;10:4-18.

Aird. The role of the endothelium in severe sepsis and multiple organ dysfunction syndrome. Blood. 2003;101:3765-77.

Yuyun, et al. Endothelial dysfunction, endothelial nitric oxide bioavailability, tetrahydrobiopterin, and 5-methyltetrahydrofolate in cardiovascular disease. Where are we with therapy? Microvasc Res. 2018;119:7-12.

Cecconi, et al. Early Predictors of Clinical Deterioration in a Cohort of 239 Patients Hospitalized for Covid-19 Infection in Lombardy, Italy. J Clin Med. 2020;9:1548.

Cui, et al. Prevalence of venous thromboembolism in patients with severe novel coronavirus pneumonia. J Thromb Haemost. 2020;18:1421-4.

Tibirica, et al. Importance of the evaluation of systemic microvascular flow and reactivity in critically ill patients with coronavirus disease 2019—COVID-19. Microvasc Res. 2020;131:104028.

Colbert, et al. Endothelial and Microcirculatory Function and Dysfunction in Sepsis. Clin Chest Med. 2016;37:263-75.

Carlton, et al. Markers of Endothelial Dysfunction and Cytokines in High-Risk Pediatric Patients with Severe Sepsis. Am J Respir Crit Care Med. 2020;201:380-4.

Handa, et al. Role of endothelial nitric oxide synthase-derived nitric oxide in activation and dysfunction of cerebrovascular endothelial cells during early onsets of sepsis. Am J Physiol Heart Circ Physiol. 2008;295:H1712-9.

Ince C, et al. The endothelium in sepsis. Shock. 2016;45(3):259-70.

Gielis et al., "Pathogenetic role of eNOS uncoupling in cardiopulmonary disorders", Free Radical Biology & Medicine, 2011, 50:765-776.

Martel, et al. Could nasal nitric oxide help to mitigate the severity of COVID-19? Microbes Infect. 2020;22:168-71.

Horowitz, et al. Three novel prevention, diagnostic, and treatment options for COVID-19 urgently necessitating controlled randomized trials. Med Hypotheses. 2020;143:109851.

Isidori, et al. Targeting the NO-cGMP-PDE5 pathway in COVID-19 infection. Andrology. 2020:33-38.

Rogosnitzky, et al. Delivering Benefits at Speed Through Real-World Repurposing of Off-Patent Drugs: The COVID-19 Pandemic as a Case in Point. JMIR Public Health Surveill. 2020;6:e19199: p. 1-p. 7.

Green. Covid-19 accelerates endothelial dysfunction and nitric oxide deficiency. Microbes Infect. 2020;22:149-50.

Neill, et al. Quantitative RT-PCR comparison of the urea and nitric oxide cycle gene transcripts in adult human tissues. Molecular genetics and metabolism. 2009;97:121-7.

Erez, et al. Requirement of argininosuccinate lyase for systemic nitric oxide production. Nature medicine. 2011;17:1619-26.

Smith, et al. Nitric oxide precursors and congenital heart surgery: a randomized controlled trial of oral citrulline. The Journal of thoracic and cardiovascular surgery. 2006;132:58-65.

Barr. Clinical Study Report: Phase IB Single Blind, Randomized, Placebo Controlled Clinical Trial to Determine the Pharmacokinetics and Safety of a Revised Protocol of Intravenous L-Citrulline Versus Placebo in Children Undergoing Cardiopulmonary Bypass. Revised Protocol CIT-002-01; Version 4.1. Asklepion Pharmaceuticals LLC; 2016.

Gavriilaki et al., "Endothelial Dysfunction in COVID-19: Lessons Learned from Coronaviruses", Curr Hypertens Rep., 2020, 22:63.

* cited by examiner

ACTION OF L-CITRULLINE TO PREVENT OR TREAT ENDOTHELIAL DYSFUNCTION

CROSS-REFERENCE TO RELATED APPLICATIONS

This application claims priority to U.S. Provisional Application No. 63/213,600, filed Jun. 22, 2021, the disclosure of which is hereby incorporated by reference in its entirety.

FIELD OF THE INVENTION

This invention provides methods for treating endothelial dysfunction in a patient by administering an effective amount of citrulline to the patient. The patients may be suffering from acute respiratory distress syndrome (ARDS), sepsis, or infection by COVID-19 (Coronavirus Disease 2019); COVID-19 patients may be at risk of developing endothelial dysfunction, or they may be experiencing endothelial dysfunction. The effective amount of citrulline is an amount sufficient to reduce the uncoupling of endothelial nitric oxide synthase (eNOS) or an amount sufficient to reduce the formation of free radicals. Citrulline may be administered orally; intravenously; or both orally and intravenously in a sequential manner. Sequential administration of citrulline may be in three phases, such as (a) an initial phase in which citrulline is administered orally, (b) an intermediate phase wherein citrulline is administered intravenously, and (c) a final phase wherein citrulline is administered orally. The intermediate phase may be while the patient's breathing is being assisted mechanically.

BACKGROUND OF THE INVENTION

Emerging data shows that covid-19 infection does not act through some new, uniquely destructive mechanism of action. Instead, its significance and lethality arise because it combines ready transmissibility via asymptomatic or minimally symptomatic individuals with the delayed onset of a number of well-recognized pathogenetic mechanisms. Viruses produce disease through direct cytopathic effects upon cells, by eliciting pathologic host responses that in turn damage cells and organs, or, as in the case of covid-19, via both mechanisms, with abnormal host responses predominating for covid-19. In the case of covid-19, Li and co-workers have proposed the term "viral sepsis" to describe this phenomenon.[1]

General Features of Covid-19 Infection

The typical clinical course of fatal covid-19 infection consists of 3 to 7 days of mild cough and fever with other flu-like symptoms. However, unlike patients with the flu, certain covid-19 patients, particularly those with at least one comorbidity such as diabetes, hypertension, chronic obstructive pulmonary disease, or obesity, then decompensate and present to the emergency room with respiratory distress.[2]

Autopsy series from a number of sites is generally consistent in defining the scope of the disease mechanisms operative in covid-19 infection [2-6] The consistent findings are:

An acute respiratory distress syndrome (ARDS) picture characterized by
Diffuse alveolar damage with fibrin deposition
Formation of hyaline membranes
Pulmonary hemorrhage
Pulmonary microthrombi
Infiltration by platelets and megakaryocytes, marked
Type-2 pneumocytes, desquamated, with viral cytopathic effect
Pulmonary edema
Capillary thickening
Pulmonary thromoboembolism (some cases)
Abnormal microangiogenesis
The heart is also affected:
Right ventricular dilatation[2]
Cardiomegaly, some cases
Degeneration of individual myocytes
Lymphocytic infiltrate, variable, CD3+
Microvascular dysfunction with endothelitis Microthrombi are found occasionally in the liver, spleen, and other organs. In addition, the spleen regularly shows expansion of the red pulp by a lymphoplasmacytic infiltrate with diminution of the white pulp, which normally carries out immunologic functions. The significance of this change is still being investigated.

Right heart afterload has received little attention in discussions of covid-19 disease, perhaps because of the difficulties of assessing right heart pressures absent a right heart catheter. However, the regular finding of right ventricular dilatation by Fox[2] and colleagues, along with the echocardiographic evidence reported by Mahmoud-ElSayed and co-workers[7] provide strong evidence for increased pulmonary afterload. Although Mahmoud-Elsayed's echocardiographic study was unable to identify outright pulmonary hypertension, it did identify right ventricular dysfunction which the authors attributed to pulmonary vasoconstriction. Thus, either pulmonary vasoconstriction or pulmonary hypertension may play a role in severe covid-19 infection.

The Role of Vascular Endothelium in Covid-19 Infection

Aside from the pulmonary findings, endothelial damage with abnormal function and thrombosis are two of the most commonly described features linked to the pathogenesis of covid-19 disease. Ackermann and colleagues[4] demonstrated severe endothelial injury in the lungs of covid-19 patients with endothelial cell membrane disruption. The lungs further showed widespread microangiopathy and capillary occlusion. Increased angiogenesis was also observed, perhaps as a reparative and compensatory mechanism. Endothelial injury also occurs in the heart. Chen et al.[8], noting the extent of endothelial damage, hypothesized that the true target might be pericytes expressing high levels of the ACE2 receptor to which covid-19 binds. Damage to the pericytes leads, then, in turn to collateral damage of the endothelium and microvasculature. Endothelial injury associated with covid-19 infection has also been reported in the small bowel[9], suggesting that endothelial damage plays a general role in covid-19 infections.

The consequences of endothelial injury and dysfunction in covid-19 appear to underlie many of the immunologic and thrombotic complications of covid-19 infection[1,10-12]. In many ways, the situation resembles more familiar forms of sepsis, where endothelial injury is associated with thrombosis and disseminated intravascular coagulation[13,14]. The importance of endothelial dysfunction in the genesis of covid-19 associated coagulopathies is underscored by the fact that angiopoietin-2 is an important predictor of poor outcome in covid-19 infections[15]. Likewise, the importance of the associated disseminated intravascular coagulation is underscored by the strong negative prognostic implications of increased D-dimer levels[16,17].

Nitric Oxide and Endothelial Injury

Endothelial injury and activation is increasingly recognized as the central event underlying the often fatal sequelae of covid-19 infection[4,9,10,18]. In this regard, it is entirely analogous to sepsis, where endothelial dysfunction also plays a central role[11,13,14,19-22]. Close examination of the features of endothelial dysfunction in sepsis, described in the cited references, shows that they are virtually identical to analogous features found in covid-19 infection.

Gustafson et al.[18], incorporated herein by reference, discusses the complexity of the role of activated, or dysfunctional, endothelium in covid-19 infection, and provides At a high level, the endothelium is central to vascular permeability, inflammation, hemostasis, and microvascular function. A quiescent endothelium facilitates normal responses to angiogenic signaling, facilitates controlled immune surveillance, and provides homeostatic cues for coagulation. A proposed pathobiology of the activated endothelium during severe acute respiratory syndrome coronavirus-2 (SARS-CoV-2 infection) contemplates chronic activation of the endothelium, marked by stark upregulation of P-selectin, E-Selectin, ICAM-1 (intercellular adhesion molecule), and ACE2 (angiotensin-converting enzyme 2), along with their respective soluble forms. The subsequent loss of tight junction expression expedites edema and facilitates enhanced recruitment, attachment, and extravasation of immune cells across the vascular endothelium. Disruption of coagulation cues through the loss of heparan, DDP-4, and t-PA (tissue-type plasminogen activator) and secretion of vWF (von Willebrand Factor) exacerbates endothelial injury and induces coagulopathies. Further disruption of endothelial phenotype results in local reductions of secreted NO, increases in secreted reactive oxygen species (ROS), and enhanced Ang-II secretion. SARS-CoV-2 reduces ACE2 availability further propagating endothelial dysfunction. While intended to assist in infection control, innate and adaptive immune responses can instead induce a storm of chemokines and cytokines, which further propagates underlying inflammation and dysfunction. Each of these systems has been implicated in the pathogenesis of covid-19 disease. The key point of this proposal is that dysregulation of each of these functions can be explained by dysfunction at a central point of convergence, the vascular endothelium.

Abnormal coagulation is a hallmark of covid-19 disease. This is so much the case that elevated D-dimer measurements are a consistent, strong predictor of poor outcome in a number of covid-19 studies[16,23,24]. The propensity toward gross and microscopic thrombosis, well-documented in the previously cited autopsy series, provides further evidence of the adverse impact of the disseminated intravascular coagulation-like picture produced by covid-19[2-6]. Erosion of the surface glycocalyx as well as abnormal activation of the coagulation system by a variety of mechanisms appear to be etiologic.

Disruption of the microcirculation is another major sequela of covid-19 infection and is thought to have adverse clinical implications[25]. A completely analogous situation pertains in sepsis[26], where endothelial changes can lead to diffuse pulmonary vasoconstriction with pulmonary hypertension, as is seen with acute lung injury. The situation is complex, since the constrictive and thrombotic changes in the microvasculature are also accompanied by the growth of new vessels[4]. Angiogenesis seems to be a regular feature of the pathophysiology of covid-19 infection since angiopoietin-2 levels are a strong predictor of direct intensive care unit admission of covid-19 patients[15], similar to findings in pediatric patients with sepsis[27]

The Important Role of Nitric Oxide

Nitric oxide, NO, plays a central, unifying role in the numerous manifestations of endothelial dysfunction[13,19,20,22,28,29]. NO, produced in endothelial cells by endothelial nitric oxide synthase mediates vascular relaxation. Additionally, NO is antithrombotic through its ability to inhibit activation and adherence of platelets to endothelial surfaces. This action of NO can counter the tendency in sepsis toward endothelial dysfunction whose features include disruption of microcirculatory homeostasis with impairment of oxygen transport[21] and prothrombotic adhesion of platelets with antifibrinolytic activity.

Uncoupling of eNOS leads to production of free radicals by the monomeric catalytic subunit of eNOS instead of NO[13,30]. The dysregulated production of free radicals leads to tissue damage, altered vascular permeability, and other adverse consequences.

No and Covid-19 Infection

The central role of NO, or its absence, in mediation of endothelial dysfunction, thrombogenicity, microvascular tone, free radical production, and microvascular permeability in severe infections has led several workers to suggest that NO or agents that augment NO production could have therapeutic value in the treatment of covid-19 infection. Martel and co-workers[31] recently proposed that inhaled NO could be used to treat the ARDS-like features of covid-19 respiratory disease. These investigators noted the moderate success of inhaled NO on the 2002-2003 SARS agent, yielding decreased pulmonary hypertension, improved arterial oxygenation, and reduction in the spread and density of lung infiltrates. Sildenafil was also considered since it enhances NO effects; other investigators have also considered sildenafil[32-34]. Green[35] noted, "A hallmark of endothelial dysfunction and thrombotic events is suppressed endothelial nitric oxide synthetase (eNOS) with concomitant nitric oxide deficiency. In healthy vessels, the endothelium releases the vasodilator and antithrombotic factor, nitric oxide. Whereas in injured vessels, nitric oxide is impaired contributing hypertension and thrombus formation." Furthermore, a cross talk between epithelium and endothelium may mediate human alveolar-capillary injury. The pulmonary endothelial cell is an initiator and propagator of vascular disruption and as such becomes a therapeutic target. L-Citrulline is likely to preserve vessel barrier integrity and prevent vascular endothelitis due to inflammatory cell infiltration.

SUMMARY OF THE INVENTION

Treatment of covid-19 using systemic agents that can raise NO levels such as nitroglycerine were discussed by Martel[31]. Green[35] considered treatment with agents to increase NO synthesis could be an important treatment for covid-19 infections. However, none of these authors addressed how in the nitric oxide cycle controls eNOS production of NO to ensure that this cellular effector is maintained at a sufficient level to protect tissues by avoid detrimental levels of active oxygen species without reaching levels that could detrimentally effect tissues in other ways. The present inventors recognize that maintenance of circulating levels of citrulline in plasma can be used to avoid endothelial dysfunction in a safely and effectively.

This invention is directed to a method for treating endothelial dysfunction in a patient by administering an effective amount of citrulline to the patient, the effective amount of citrulline being an amount sufficient to reduce the uncoupling of endothelial nitric oxide synthase (eNOS), which is typically at least 37 µM, preferably at least 100 µM but less than 190 µM, more preferably at least 50, at least 75, 100, 120, 130, or 140 µM, and no more than 200 µM, or no more than 190, 180, 170, 160, or 150 µM. The effective amount of citrulline is an amount sufficient to reduce the formation of free radicals, which is typically accomplished by raising plasma citrulline level of the patient above about 37, 50, 100, 150, or 200 µM. Endothelial dysfunction is typically associated with thrombosis and disseminated intravascular coagulation. Patients suffering from endothelial dysfunction include patients with acute respiratory distress syndrome (ARDS), sepsis, or patients infected by COVID-19 (Coronavirus Disease 2019), particularly patients infected by COVID-19 and at risk of developing endothelial dysfunction or experiencing endothelial dysfunction. Patients experiencing endothelial dysfunction may be identified by elevated plasma levels of D-dimer, preferably above 250 ng/ml, or elevated plasma levels of angiopoietin-2.

Treatment according to this invention may be accomplished by administering citrulline orally; intravenously; or both orally and intravenously, usually in a sequential manner. In one aspect, citrulline may be administered sequentially in three phases, the three phases being (i) an initial phase in which citrulline is administered orally; (ii) an intermediate phase wherein citrulline is administered intravenously; and (iii) a final phase wherein citrulline is administered orally. The intermediate (intravenous) phase may coincide with a period when the patient's breathing is being assisted mechanically. Treatment according to this invention may comprise intravenously administered citrulline provided as a continuous infusion at about 3 mg/kg/hour to about 12 mg/kg/hour, typically as a continuous infusion at about 9 mg/kg/hour. In the initial phase, citrulline may be administered as an oral or intravenous bolus at about 100-500 mg/kg, or at about 100-300 mg/kg, or at about 150 mg/kg. The initial and the intermediate phases may be separated by 10-24 hours. Alternatively, citrulline may be administered in a manner and amount that results in reduction of D-dimer levels, preferably below 250 ng/ml, and/or reduction of angiopoietin-2 level by a detectable quantity from the elevated angiopoietin-2 level in the patient before treatment.

DETAILED DESCRIPTION OF THE EMBODIMENTS

Citrulline, NO Production, and Pulmonary Hypertension

Intravenous citrulline can serve as an important agent to increase endogenous NO production in covid-19 infection. Unlike inhaled nitric oxide, which is bioavailable only in the lung, intravenous citrulline is systemically available. Although treatment with oral citrulline was suggested by Martel[31], for a variety of reasons, therapeutic levels cannot be achieved orally.

Citrulline is produced in endothelial cells by a partial urea cycle[36] that exists in a complex with eNOS on an HSP 90 backbone bound to the caveolar membrane in endothelial cells.[37] The complete urea cycle exists in liver and gut, where it serves to detoxify ammonia. However, the partial urea cycle in other tissues serves principally to produce nitric oxide. Although arginine is the proximate NO donor, it cannot enter the synthetic complex in endothelial cells. Instead, citrulline, which is specifically transported into endothelial cells, serves as the ultimate nitric oxide donor. Increasing citrulline concentrations in the plasma can drive nitric oxide production. Stress or other physiologic reasons may cause plasma citrulline concentrations to fall to low levels fairly rapidly. This occurs in part because the half-life of citrulline in plasma is about 1 hour.

Low citrulline levels are associated with adverse effects. Smith et al.[38] found that complications of pulmonary bypass such as pulmonary hypertension in children undergoing congenital heart repair surgery only occurred in patients with low citrulline levels. These results are shown in the table below.

TABLE

| Low risk of pulmonary hypertension with high plasma citrulline | | | |
|---|---|---|---|
| Plasma citrulline 12 h postoperatively | Pulmonary hypertension absent | Pulmonary hypertension present | P value |
| <37 µmol/L | 18 | 9 | |
| >37 µmol/L | 12 | *0 | .036 |

Only patients with plasma citrulline levels below 37 micromolar developed pulmonary hypertension. None of the patients with levels above 37 micromolar developed this complication. The authors hypothesized that the occurrence of pulmonary hypertension was due to an NO deficit resulting from inadequate citrulline levels.

Correction of Low Citrulline Levels Prevents Pulmonary Hypertension

Figure 1:
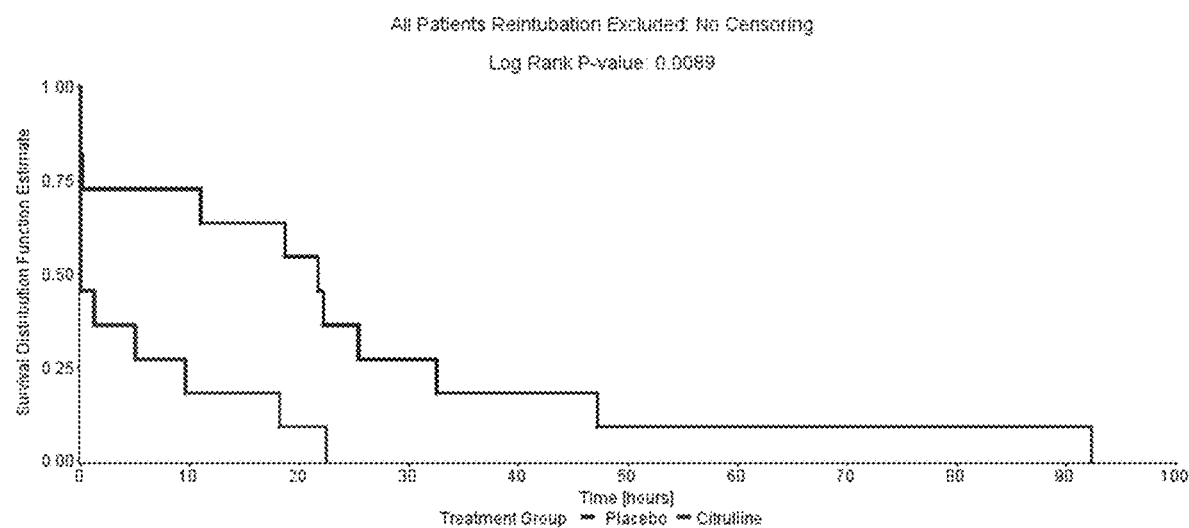
FIG. 1. Duration of mechanical ventilation therapy following cardiopulmonary bypass in citrulline treated and control patients. Wilcoxon rank-sum analysis indicates treated differs from control (p=0.0089).
Figure 2:
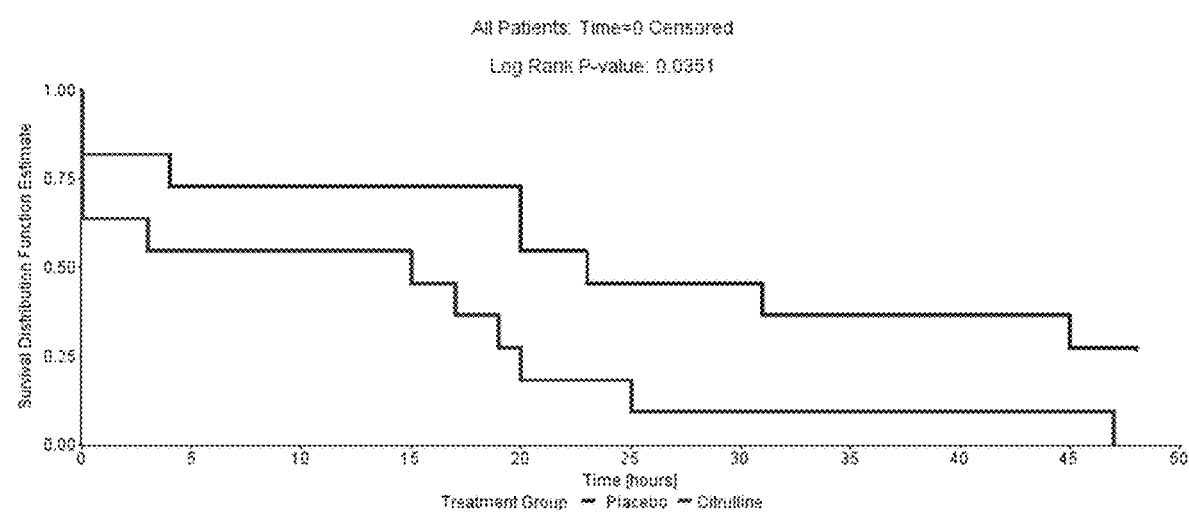
FIG. 2. Duration of inotrope therapy following cardiopulmonary bypass in citrulline treated and control patients. Wilcoxon rank-sum analysis indicates treated differs from control (p=0.0351).
Figure 3:
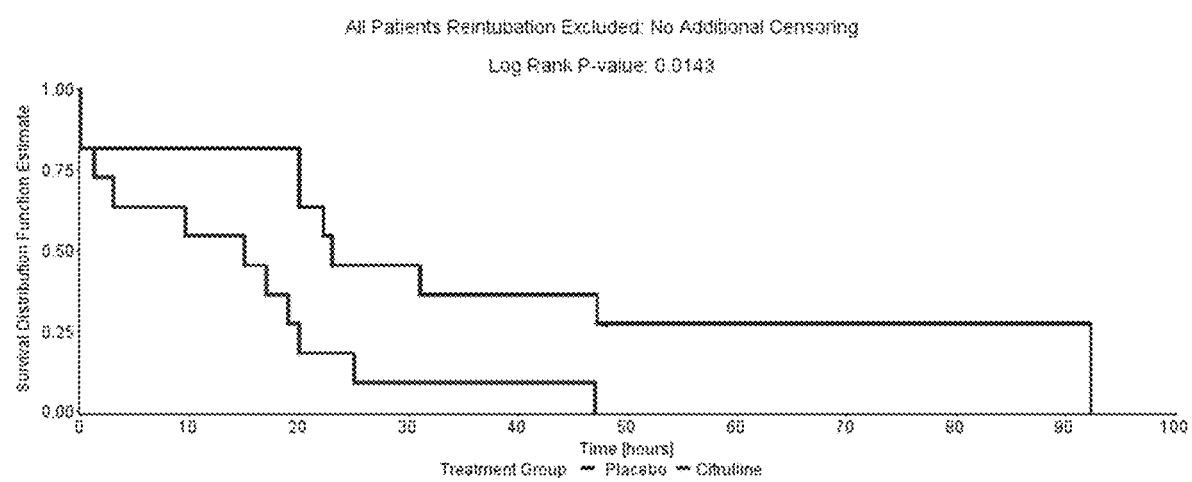
FIG. 3. Maximum of mechanical ventilation or inotrope therapy (surrogate for duration of ICU stay) following cardiopulmonary bypass in citrulline treated and control patients. Wilcoxon rank-sum analysis indicates treated differs from control (p=0.0479).

A recent study[39] carried out under IND #66,261 examined whether maintenance of plasma citrulline levels at steady state levels at or above 100 micromolar would prevent the occurrence of pulmonary complications of cardiopulmonary bypass in children undergoing congenital heart repair surgery. For pulmonary function, the endpoint was the postoperative duration of mechanical ventilation (see FIG. 1). Alternative endpoints included the duration of post-operative inotrope therapy (see FIG. 2) and the length of time in the intensive care unit (see FIG. 3). The results, shown in FIGS. 1-3, indicate that citrulline administration at the indicated dosing level prevented the complications of bypass, as indicated by both time on mechanical ventilation and duration of inotrope therapy.

Citrulline Appears Safe and the Planned Dose is Reasonable

Intravenous citrulline has proven to be safe in prior clinical studies, and its use is supported by a sound rationale. Citrulline was recently studied in a Phase III multicenter trial under IND #66,261 (NCT02891837, L-citrulline for Prevention of Sequelae of Acute Lung Injury in Pediatrics Undergoing Cardiopulmonary Bypass for Heart Defects). These studies used a dosing regimen that produced levels comparable to those contemplated herein for treatment of covid-19 patients. In this study, there were no drug-associated adverse events. It should be noted that substantially higher doses of citrulline than those contemplated herein for treatment of covid-19 patients are routinely administered to pediatric patients with urea cycle disorders with no observed adverse effects.[40] Therefore, the use of citrulline in the planned patient population is safe.

Both mechanistic considerations and clinical evidence indicate that citrulline can ameliorate the sequelae of lung injury in the cardiopulmonary bypass setting. This evidence fully justifies the use of citrulline as a therapeutic agent for covid-19 disease.

Treatment of Acute Covid-19 Patients

This invention contemplates intravenous administration of citrulline as an adjunct therapy for hospitalized covid-19 patients. Patients with detectable viral load of SARS-CoV-2 virus may be infused with citrulline in an amount and schedule to maintain serum citrulline above 37 µM, preferably above 50 µM, more preferably above 100 µM. This therapy will be directed to viremic patients, especially those with elevated levels of angiotensin-2 and/or D-dimer. Treatment according to this protocol is especially contemplated for patients requiring oxygen due to acute hypoxemic respiratory illness. Alternatively, citrulline may be administered to viremic patients who do not yet require oxygen supplementation, with the intent of preventing a transition to more severe disease with elevated levels of markers such as antgiotensin-2 and/or D-dimer. Intravenous formulation of citrulline, and the infusion protocol are within the skill of the art, particularly in view of the prior description of intravenous citrulline treatment for cardiac surgery patients and sickle cell crisis, see U.S. Pat. Nos. 10,265,286, 10,525,026, and 9,486,429, and US Published Application 20180289647, these descriptions being incorporated herein by reference.

EXAMPLES

Example I. Citrulline Treatment of Covid-19 Patients

Subjects hospitalized and requiring oxygen for an acute hypoxemic respiratory illness due to COVID-19 (SARS-CoV2) will be treated. In addition, subjects will receive standard supportive care for acute hypoxemic respiratory illness and failure. The assessment of efficacy will include collection of plasma for analysis of citrulline and arginine levels at 2 hours, 12 hours, and the alternating morning of study days. Optionally, samples may also be analyzed for D-dimer and angiopoietin-2 levels.

The assessment of efficacy will include collection of plasma for analysis of citrulline and arginine levels at 2 hours, 12 hours, and the alternating morning of hospitalization days. Additional efficacy measures will include clinical outcomes, including progression of acute lung injury and, lengths of hospital and ICU stay. The assessment of safety will include collection of hemodynamic measurements at least every 4 hours on a hospital unit.

Patients will receive an initial intravenous bolus of 20 mg/kg (to a maximum of 1500 mg) L-citrulline over 10 minutes. The infusion solution will be prepared as a 5% isotonic solution (50 mg/mL) in 5% dextrose water. Immediately after the initial bolus, a continuous intravenous infusion of L-citrulline at 9 mg/kg (max 700 mg) per hour will be administered through a dedicated intravenous line or port of a multi-lumen catheter. The infusion will continue for up to 10 days.

One effect of intravenous citrulline is to extend the length of time to an intubation event in hours from the start of study infusion. This study also demonstrates the effect of intravenous L-Citrulline to reduce the total length of all mechanical ventilation, including non-invasive modalities such as high flow nasal cannula, BiPAP and oxygen therapy.

Participant survival will be assessed at hospital discharge. ICU length of stay will be the total number of days the participant spends in the ICU from initial treatment to hospital discharge. Re-admissions to the ICU during the initial hospital stay will be added to the initial ICU length of stay in order to determine a total number of ICU days. Hospital length of stay will be calculated as the number of days from admission to hospital discharge.

REFERENCES

1. Li H, Liu L, Zhang D, et al. SARS-CoV-2 and viral sepsis: observations and hypotheses. Lancet 2020; 395:1517-20.
2. Fox S E, Akmatbekov A, Harbert J L, Li G, Quincy Brown J, Vander Heide R S. Pulmonary and cardiac pathology in African American patients with COVID-19: an autopsy series from New Orleans. Lancet Respir Med 2020.
3. Buja L M, Wolf D A, Zhao B, et al. The emerging spectrum of cardiopulmonary pathology of the coronavirus disease 2019 (COVID-19): Report of 3 autopsies from Houston, Texas, and review of autopsy findings from other United States cities. Cardiovasc Pathol 2020; 48:107233.
4. Ackermann M, Verleden S E, Kuehnel M, et al. Pulmonary Vascular Endothelialitis, Thrombosis, and Angiogenesis in Covid-19. N Engl J Med 2020.
5. Schaller T, Hirschbühl K, Burkhardt K, et al. Postmortem Examination of Patients With COVID-19. Jama 2020.
6. Wichmann D, Sperhake JP, Lütgehetmann M, et al. Autopsy Findings and Venous Thromboembolism in Patients With COVID-19. Ann Intern Med 2020.
7. Mahmoud-Elsayed H M, Moody W E, Bradlow W M, Khan-Kheil A M, Hudsmith L E, Steeds R P. Echocardiographic Findings in Covid-19 Pneumonia. Can J Cardiol 2020.
8. Chen L, Li X, Chen M, Feng Y, Xiong C. The ACE2 expression in human heart indicates new potential mechanism of heart injury among patients infected with SARS-CoV-2. Cardiovasc Res 2020; 116:1097-100.
9. Carnevale S, Beretta P, Morbini P. Direct endothelial damage and vasculitis due to SARS-CoV-2 in small bowel submucosa of CoViD-19 patient with diarrhea. J Med Virol 2020.
10. Teuwen L A, Geldhof V, Pasut A, Carmeliet P. COVID-19: the vasculature unleashed. Nat Rev Immunol 2020: 1-3.
11. Connors J M, Levy J H. COVID-19 and its implications for thrombosis and anticoagulation. Blood 2020; 135: 2033-40.
12. Iba T, Levy J H, Levi M, Connors J M, Thachil J. Coagulopathy of Coronavirus Disease 2019. Crit Care Med 2020.
13. Boisramé-Helms J, Kremer H, Schini-Kerth V, Meziani F. Endothelial dysfunction in sepsis. Curr Vasc Pharmacol 2013; 11:150-60.
14. Pons S, Arnaud M, Loiselle M, Arrii E, Azoulay E, Zafrani L. Immune Consequences of Endothelial Cells' Activation and Dysfunction During Sepsis. Crit Care Clin 2020; 36:401-13.
15. Smadja D M, Guerin C L, Chocron R, et al. Angiopoietin-2 as a marker of endothelial activation is a good predictor factor for intensive care unit admission of COVID-19 patients. Angiogenesis 2020:1-10.
16. Li C, Hu B, Zhang Z, et al. D-dimer triage for COVID-19. Acad Emerg Med 2020.

17. Cummings M J, Baldwin M R, Abrams D, et al. Epidemiology, clinical course, and outcomes of critically ill adults with COVID-19 in New York City: a prospective cohort study. Lancet 2020; 395:1763-70.
18. Gustafson D, Raju S, Wu R, et al. Overcoming Barriers: The Endothelium As a Linchpin of Coronavirus Disease 2019 Pathogenesis? Arterioscler Thromb Vasc Biol 2020: Atvbaha120314558.
19. Cyr A R, Huckaby L V, Shiva S S, Zuckerbraun B S. Nitric Oxide and Endothelial Dysfunction. Crit Care Clin 2020; 36:307-21.
20. Tousoulis D, Kampoli A M, Tentolouris C, Papageorgiou N, Stefanadis C. The role of nitric oxide on endothelial function. Curr Vasc Pharmacol 2012; 10:4-18.
21. Aird W C. The role of the endothelium in severe sepsis and multiple organ dysfunction syndrome. Blood 2003; 101:3765-77.
22. Yuyun M F, Ng L L, Ng G A. Endothelial dysfunction, endothelial nitric oxide bioavailability, tetrahydrobiopterin, and 5-methyltetrahydrofolate in cardiovascular disease. Where are we with therapy? Microvasc Res 2018; 119:7-12.
23. Cecconi M, Piovani D, Brunetta E, et al. Early Predictors of Clinical Deterioration in a Cohort of 239 Patients Hospitalized for Covid-19 Infection in Lombardy, Italy. J Clin Med 2020; 9.
24. Cui S, Chen S, Li X, Liu S, Wang F. Prevalence of venous thromboembolism in patients with severe novel coronavirus pneumonia. J Thromb Haemost 2020; 18:1421-4.
25. Tibirica E, De Lorenzo A. Importance of the evaluation of systemic microvascular flow and reactivity in critically ill patients with coronavirus disease 2019—COVID-19. Microvasc Res 2020; 131:104028.
26. Colbert J F, Schmidt E P. Endothelial and Microcirculatory Function and Dysfunction in Sepsis. Clin Chest Med 2016; 37:263-75.
27. Carlton E F, McHugh W M, McDonough K, Sturza J, Desch K, Cornell T T. Markers of Endothelial Dysfunction and Cytokines in High-Risk Pediatric Patients with Severe Sepsis. Am J Respir Crit Care Med 2020; 201: 380-4.
28. Handa O, Stephen J, Cepinskas G. Role of endothelial nitric oxide synthase-derived nitric oxide in activation and dysfunction of cerebrovascular endothelial cells during early onsets of sepsis. Am J Physiol Heart Circ Physiol 2008; 295:H 1712-9.
29. Ince C, Mayeux P R, Nguyen T, et al. THE ENDOTHELIUM IN SEPSIS. Shock 2016; 45:259-70.
30. Gielis J F, Lin J Y, Wingler K, Van Schil P E, Schmidt H H, Moens A L. Pathogenetic role of eNOS uncoupling in cardiopulmonary disorders. Free Radic Biol Med 2011; 50:765-76.
31. Martel J, Ko Y F, Young J D, Ojcius D M. Could nasal nitric oxide help to mitigate the severity of COVID-19? Microbes Infect 2020; 22:168-71.
32. Horowitz R I, Freeman P R. Three novel prevention, diagnostic, and treatment options for COVID-19 urgently necessitating controlled randomized trials. Med Hypotheses 2020; 143:109851.
33. Isidori A M, Giannetta E, Pofi R, et al. Targeting the NO-cGMP-PDE5 pathway in COVID-19 infection. Andrology 2020.
34. Rogosnitzky M, Berkowitz E, Jadad A R. Delivering Benefits at Speed Through Real-World Repurposing of Off-Patent Drugs: The COVID-19 Pandemic as a Case in Point. JMIR Public Health Surveill 2020; 6:e19199.
35. Green S J. Covid-19 accelerates endothelial dysfunction and nitric oxide deficiency. Microbes Infect 2020; 22:149-50.
36. Neill M A, Aschner J, Barr F, Summar M L. Quantitative RT-PCR comparison of the urea and nitric oxide cycle gene transcripts in adult human tissues. Molecular genetics and metabolism 2009; 97:121-7.
37. Erez A, Nagamani S C, Shchelochkov O A, et al. Requirement of argininosuccinate lyase for systemic nitric oxide production. Nature medicine 2011; 17:1619-26.
38. Smith H A, Canter J A, Christian K G, et al. Nitric oxide precursors and congenital heart surgery: a randomized controlled trial of oral citrulline. The Journal of thoracic and cardiovascular surgery 2006; 132:58-65.
39. Barr F E. Clinical Study Report: Phase IB Single Blind, Randomized, Placebo Controlled Clinical Trial to Determine the Pharmacokinetics and Safety of a Revised Protocol of Intravenous L-Citrulline Versus Placebo in Children Undergoing Cardiopulmonary Bypass. Revised Protocol CIT-002-01; Version 4.1. Asklepion Pharmaceuticals LLC; 2016.
40. Summar M. Personal Communication. 2019.

What is claimed is:

1. A method for treating endothelial dysfunction in a patient, the method comprising administering an effective amount of citrulline to the patient, wherein the effective amount of citrulline is an amount sufficient to reduce the uncoupling of endothelial nitric oxide synthase (eNOS) and/or an amount sufficient to reduce the formation of free radicals;
   wherein the patient experiencing endothelial dysfunction has plasma levels of D-dimer above 250 ng/mL; and/or
   wherein the effective amount of citrulline is sufficient to reduce plasma level of angiopoietin-2 by a detectable amount.

2. The method of claim 1, wherein the endothelial dysfunction is associated with thrombosis and disseminated intravascular coagulation.

3. The method of claim 1, wherein the patient has acute respiratory distress syndrome (ARDS), sepsis, or is infected by COVID-19 (Coronavirus Disease 2019).

4. The method of claim 1, wherein the patient experiencing endothelial dysfunction has plasma levels of D-dimer above 250 ng/ml.

5. The method of claim 1, wherein citrulline is administered orally; intravenously; or both orally and intravenously in a sequential manner.

6. The method of claim 5, wherein citrulline is administered orally.

7. The method of claim 5, wherein citrulline is administered intravenously.

8. The method of claim 5, wherein citrulline is administered sequentially in three phases, the three phases being
   a. an initial phase in which citrulline is administered orally;
   b. an intermediate phase wherein citrulline is administered intravenously; and
   c. a final phase wherein citrulline is administered orally.

9. The method of claim 8 wherein, in the intermediate phase, the patient's breathing is being assisted mechanically.

10. The method of claim 1, wherein citrulline is administered in an amount effective to raise plasma citrulline level of the patient above about 37 μM/L.

11. The method of claim 1, wherein citrulline is administered in an amount effective to raise plasma citrulline level of the patient above about 100 μM/L.

12. The method of claim 7, wherein intravenously administered citrulline is provided as a continuous infusion at about 3 mg/kg/hour to about 12 mg/kg/hour.

13. The method of claim 12, wherein intravenously administered citrulline is provided as a continuous infusion at about 9 mg/kg/hour.

14. The method of claim 8, wherein, in the initial phase, citrulline is administered as a bolus at about 100-500 mg/kg.

15. The method of claim 14, wherein the bolus of citrulline is at about 100-300 mg/kg.

16. The method of claim 15, wherein the bolus of citrulline is at about 150 mg/kg.

17. The method of claim 8, wherein the initial and the intermediate phases are separated by 10-24 hours.

18. The method of claim 1, wherein the effective amount of citrulline is sufficient to reduce plasma level of angiopoietin-2 by a detectable amount.

19. A method for treating endothelial dysfunction in a patient, the method comprising administering an effective amount of citrulline to the patient, wherein the effective amount of citrulline is an amount sufficient to reduce the uncoupling of endothelial nitric oxide synthase (eNOS) and/or an amount sufficient to reduce the formation of free radicals, the method including both a phase in which citrulline is administered orally and a phase in which citrulline is administered intravenously, these phases occurring in a sequential manner.

20. The method of claim 19, wherein citrulline is administered in an amount effective to raise plasma citrulline level of the patient above about 37, 50, 100, 150, or 200 µM/L.

* * * * *